United States Patent [19]
Sarantakis

[11] 3,937,695
[45] Feb. 10, 1976

[54] P-GLU-TRP-SER-TYR-D-LYS-LEU-ARG-PRO-GLY-NH$_2$ AND INTERMEDIATES
[75] Inventor: Dmitrios Sarantakis, West Chester, Pa.
[73] Assignee: American Home Products Corporation, New York, N.Y.
[22] Filed: Nov. 4, 1974
[21] Appl. No.: 520,515

[52] U.S. Cl. .................. 260/112.5 LH; 424/177
[51] Int. Cl.$^2$ ................ C07C 103/52; A61K 37/00
[58] Field of Search ....................... 260/112.5

[56] References Cited
UNITED STATES PATENTS
3,842,065 10/1974 Rees ........................ 260/112.5
3,855,199 12/1974 Foell et al. ................. 260/112.5

OTHER PUBLICATIONS

Fujino et al.: *Biochem. Biophys. Res. Comm.*, 57, 1248–1256 (1974).

*Primary Examiner*—Lewis Gotts
*Assistant Examiner*—Reginald J. Suyat

[57] ABSTRACT

D-Lys$^6$-des-His$^2$-LRF, is described as well as its synthesis by solid phase techniques and novel intermediates formed by such synthesis. The novel nonapeptide exhibits anti-ovulatory activity in mammals.

5 Claims, No Drawings

P-GLU-TRP-SER-TYR-D-LYS-LEU-ARG-PRO-GLY-NH₂ AND INTERMEDIATES

This invention relates to the novel nonapeptide p-Glu-Trp-Ser-Tyr-D-Lys-Leu-Arg-Pro-Gly-NH$_2$, its process of manufacture and novel intermediates formed in such synthesis.

The luteinizing hormone releasing factor (hereafter called LRF) is the decapeptide, L-(5-oxoprolyl)-L-histidyl-L-tryptophyl-L-seryl-L-tyrosyl-glycyl-L-leucyl-L-arginyl-L-prolyl-glycine amide. This decapeptide is secreted by the hypothalamus and carried to the adenohypophysis where it stimulates the release of the luteinizing hormone and the follicle stimulating hormone. The present invention concerns itself with structural modifications of LRF in which the amino acid in the two position has been omitted (i.e. His) and the glycine in the six position of the peptide chain has been replaced by D-lysine. Heretofore, Vale et al., Science 176, pp 933 (1972) have described a nonapeptide of the sequence p-Glu-Trp-Ser-Tyr-Gly-Leu-Arg-Pro-Gly-NH$_2$, this peptide being an analog of LRF in which histidine has been omitted. Vilchez-Martinez et al., *Endocrinology*, 95, 213 (1974) describe des-His$^2$-des-Gly$^{10}$-LRF ethyl amide and its inhibition of ovulation. Copending application Ser. No. 472,269 filed May 22, 1974, now U.S. Pat. No. 3,896,104, describes D-Lys$^6$-LRF as increasing and regulating fertility and Fujino et al., *Biochemical and Biophysical Research Communications*, 49 No. 3, pp 698–705 (Nov. 1972) describe a substantial number of LRF analogs that have been synthesized.

The novel peptides of the present invention are represented by the compounds of the formula:

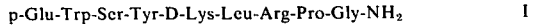

p-Glu-Trp-Ser-Tyr-D-Lys-Leu-Arg-Pro-Gly-NH$_2$    I and its non-toxic acid addition salts. All chiral amino acid residues indentified in formula I supra, and the other formulas hereinafter are of the natural or L-configuration unless specified otherwise.

Also contemplated within the scope of the present invention are intermediates of the formula

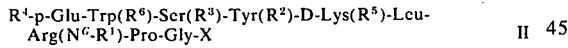

R$^4$-p-Glu-Trp(R$^6$)-Ser(R$^3$)-Tyr(R$^2$)-D-Lys(R$^5$)-Leu-Arg(N$^G$-R$^1$)-Pro-Gly-X    II wherein:

N$^G$ means the side chain nitrogen atoms of arginine;

R$^1$ is a protecting group for the N$^\delta$, N$^\omega$ and N$^{\omega'}$ nitrogen atoms of arginine selected from the group consisting of nitro, tosyl, benzyloxycarbonyl, adamantyloxycarbonyl and tert-butyloxycarbonyl; or R$^1$ is hydrogen which means there are no protecting groups on the side chain nitrogen atoms of arginine. Where the protecting group is nitro or tosyl, the protection is on either one of the N$^\omega$, N$^{\omega'}$ nitrogens and in the case of benzyloxycarbonyl, or adamantyloxycarbonyl, the protection is on the N$^\delta$ nitrogen and either one of the N$^\omega$, N$^{\omega'}$ nitrogen atoms;

R$^2$ is a protecting group for the phenolic hydroxyl group of tyrosine selected from the group consisting of tetrahydropyranyl, tert-butyl, trityl, benzyl, 2,6-dichlorobenzyl, benzyloxycarbonyl and 4-bromobenzyloxycarbonyl. The preferred protecting group is 2,6-dichlorobenzyl; or R$^2$ is hydrogen which means there is no protecting group on the phenolic hydroxy function;

R$^3$ is a protecting group for the alcoholic hydroxyl group of serine and is selected from the group consisting of acetyl, benzoyl, tetrahydropyranyl, tert-butyl, trityl, benzyl and 2,6-dichlorobenzyl; or R$^3$ is hydrogen which means there is no protecting group on the alcoholic oxygen atom. Preferably R$^3$ is benzyl;

R$^4$ is preferably hydrogen but may also be an α-amino protecting group. The α-amino protecting group contemplated by R$^4$ are those known to be useful in the art in the step-wise synthesis of polypeptides. Among the classes of α-amino protecting groups covered by R$^4$ are (1) acyl type protecting groups illustrated by the following: formyl, trifluoroacetyl, phthalyl, toluenesulfonyl (tosyl), nitrophenylsulfenyl, etc.; (2) aromatic urethan type protecting groups illustrated by benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl; (3) aliphatic urethan protecting groups illustrated by tert-butyloxycarbonyl, diisopropylmethoxycarbonyl, isopropylcarbonyl, allyloxycarbonyl; (4) cycloalkyl urethan type protecting groups illustrated by cyclopentyloxycarbonyl, adamantyloxycarbonyl, cyclohexyloxycarbonyl and d-isobornyloxycarbonyl; (5) thio urethan type protecting groups such as phenylthiocarbonyl; (6) alkyl type protecting groups as illustrated by triphenylmethyl (trityl), benzyl; (7) trialkylsilane groups such as trimethylsilane. The preferred α-amino protecting group defined by R$^4$ are selected from the class consisting of tert-butyloxycarbonyl, tert-amyloxycarbonyl and benzyloxycarbonyl;

R$^5$ is a protecting group for the side chain amino substituent of lysine or R$^5$ is hydrogen which means there is no protecting group on the side chain amino substituent. Illustrative of suitable side chain amino protecting groups are chlorobenzyloxycarbonyl, benzyloxycarbonyl, tosyl, t-amyloxycarbonyl, t-butyloxycarbonyl, etc. The selection of such a side chain amino protecting group is not critical except that it must be one which is not removed during cleavage of the α-amino protecting group during the synthesis until the peptide of the desired amino acid sequence is obtained. Hence, the α-amino protecting and side chain amino protecting group cannot be the same;

R$^6$ is hydrogen or a protecting group for the NH group on the indole ring such as formyl; Preferably R$^6$ is hydrogen.

In formula II at least one of R$^1$, R$^2$, R$^3$, R$^5$ or R$^6$ is a protecting group.

X is selected from the group consisting of NH$_2$, OH, O—(lower)alkyl in which (lower)alkyl is C$_1$ through C$_6$ (e.g. methyl, ethyl, pentyl, isopropyl, hexyl, etc.), O-benzyl and an anchoring bond used in solid phase peptide synthesis linked to a solid polystyrene resin support represented by one of the formulas:

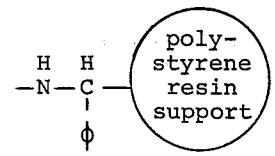

(III)

and

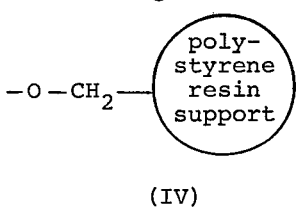

(IV)

The polystyrene resin support is preferably a copolymer of styrene with about 1 to 2% divinyl benzene as a cross linking agent which causes the polystyrene polymer to be completely insoluble in certain organic solvents. The polystyrene polymer is composed of long alkyl chains bearing a phenyl ring on every second carbon and the terminal amino acid residue (Gly) is joined through a covalent carbon to carbon bond to these phenyl rings. The alkyl chains are cross linked at approximately every fiftieth carbon by p-diethylphenyl residues derived from divinyl benzene. In formula (III) the symbol $\phi$ means phenyl.

In selecting a particular side chain protecting group to be used in the synthesis of the peptides of formula (I), the following rules should be followed: (a) the protecting group must be stable to the reagent and under the reaction conditions selected for removing the $\alpha$-amino protecting group at each step of the synthesis, (b) the protecting group must retain its protecting properties (i.e. not be split off under coupling conditions), and (c) the side chain protecting group must be removable upon the completion of the synthesis containing the desired amino acid sequence under reaction conditions that will not alter the peptide chain.

Illustrative of pharmaceutically acceptable, non-toxic salts of formula I are hydrochloride, hydrobromide, sulfate, phosphate, maleate, acetate, citrate, benzoate, succinate, malate, ascorbate, and the like.

The nonapeptides of formulas (I) and (II) are prepared using solid phase synthesis. The synthesis is commenced from the C-terminal end of the peptide using an $\alpha$-amino protected resin. Such a starting material can be prepared by attaching an $\alpha$-amino protected glycine to a benzhydrilamine resin, a chloromethylated resin or a hydroxymethyl resin, the former being preferred. The preparation of benzhydrilamine resin is described by P. Rivaille et al., Helv. 54, 2772 (1971) and the preparation of the hydroxymethyl resin is described by Bodanszky et al., Chem. Ind (London) 38, 1597–98 (1966). A chloromethylated resin is commercially available from Bio Rad Laboratories Richmond, California and the preparation of such a resin is described by Stewart et al., "Solid Phase Peptide Synthesis" (Freeman & Co. San Francisco 1969) Chapter 1, pp 1–6. In using the benzhydrilamine resin an amide anchoring bond is formed with the $\alpha$-amino protected glycine as follows:

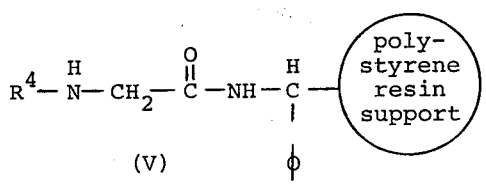

(V)

This permits the C-terminal amide function to be obtained directly after the amino acid sequence in the synthesis is complete by cleaving off the resin support to form the glycine amide at the C-terminal portion of the desired peptide of formula (I). When the other resins are used, the anchoring bond is the benzylester group as defined supra in formula (IV), which after cleavage of the peptide from the resin support must be converted to the C-terminal amide. The preferred procedure is to ammonolyse the protected peptide off the resin and then remove the protecting group by hydrogenolysis or by hydrogen fluoride cleavage. An alternate procedure would be to cleave by transesterification with methanol/(Et)$_3$N and then convert the resulting ester into an amide and subsequently deprotect as described above. See J. M. Stewart "Solid Phase Peptide Synthesis", pg. 42–46 (Freeman & Co. San Francisco 1969).

The $\alpha$-amino protected glycine is coupled to the benzhydrilamine resin with the aid of a carboxyl group activating compound such as dicyclohexylcarbodiimide (DCC). Following the coupling of the $\alpha$-amino protected glycine to the resin support, the $\alpha$-amino protecting group is removed such as by using trifluoroacetic acid in methylene chloride, trifluoroacetic acid alone or HCl in dioxane. The deprotection is carried out at a temperature between about 0°C and room temperature. Other standard cleaving reagents and conditions for removal of specific $\alpha$-amino protecting groups may be used as described in Schroder & Lubke, "The Peptides", 1 72–75 (Academic Press 1965). After removal of the $\alpha$-amino protecting group the remaining $\alpha$-amino protected amino acids are coupled step-wise in the desired order to obtain a compound of formula (I). However, as an alternate to adding each amino acid separately to the reaction, some of them may be coupled prior to addition of the solid phase reactor. If the C-terminal end of the peptide unit is represented by glycine or proline and the coupling is carried out with DCC, a minimum of racemization is encountered with proline and no problems are encountered with glycine which has no asymmetric centre. Each protected amino acid or amino acid sequence, is introduced into the solid phase reactor in about a four-fold excess and the coupling is carried out in a medium of dimethylformamide: methylene chloride (1:1) or in dimethylformamide or methylene chloride alone. In cases where incomplete coupling occurred the coupling procedure is repeated before removal of the $\alpha$-amino protecting group, prior to the coupling of the next amino acid to the solid phase reactor. The success of the coupling reaction at each stage of the synthesis is monitored by the ninhydrin reaction as described by E. Kaiser et al., Analyt. Biochem, 34, 595 (1970).

After the desired amino acid sequence has been synthesized, the peptide is removed from the resin support by treatment with a reagent such as hydrogen fluoride which not only cleaves the peptide from the resin but also cleaves all remaining side chain protecting groups and the $\alpha$-amino protecting group (if present) on pyroglutamic acid to obtain directly a compound of formula I in the case where the benzhydrilamine resin was used. Where a chloromethylated resin is used the peptide may be separated from the resin by methanolysis after which the recovered product is chromatographed on silica gel and the collected fraction subject to ammonalysis to convert the methyl ester to the C-terminal amide. Any side chain protecting group may then be cleaved as previously described or by other procedures such as catalytic reduction (e.g. Pd on C) using conditions which will keep the Trp moiety intact. When using hydrogen fluoride for cleaving, anisole is included in the reaction vessel to prevent the destruction of labile amino acid (e.g. tryptophan).

The solid phase synthesis procedure discussed supra is well known in the art and has been essentially described by M. Monahan et al., *C. R. Acad. Sci.*, Paris, 273, 508 (1971).

The nomenclature used for peptides is described by Schroder & Lubke, supra, pp viii-xxix and in *Biochemistry* 11, 1726–1732 (1972).

The following examples are illustrative of the preparation of the compounds of formulas I and II.

EXAMPLE 1

L-Pyroglutamyl-L-tryptophyl-O-benzyl-L-seryl-O-2,6-dichlorobenzyl-L-tyrosyl-N$^\epsilon$-2-chlorobenzyloxycarbonyl-D-lysyl-L-leucyl-N$^g$-tosyl-L-arginyl-L-prolyl-glycyl benzhydrilamine resin Benzhydrilamine hydrochloride resin (4 g) in a Merrifield vessel of 300 ml capacity is washed with methylene chloride (three times), treated with 15% triethylamine in methylene chloride (two times for 10 minutes each), and then washed with methylene chloride again (five times). A solution of t-Boc-glycine (0.87 g, 5 m moles) in a mixture of methylene chloride and dimethylformamide (3:1) is added to the vessel and shaken for 5 minutes. Diisopropylcarbodiimide (0.88 ml, 5.5 m moles) is added in two portions over a one hour period. After 4 hours, the reaction mixture is filtered, washed with dimethylformamide, and the vessel recharged in the above manner with t-Boc-glycine and diisopropylcarbodiimide. Sixteen hours later, the reaction mixture is filtered and washed with dimethylformamide, 15% triethylamine in dimethylformamide, dimethylformamide (three times), and methylene chloride (five times), and a sample is dried in vacuo at 40°C. The resin is found to be substituted to the extent of 0.43 m moles of t-Boc-glycine per gram of resin.

Deprotection and neutralization of the glycine residue is carried out as follows: (a) 1:1 methylene chloride and trifluoroacetic acid containing 5% ethanedithiol (two times for 15 minutes each); (b) methylene chloride wash; (c) dimethylformamide wash; (d) 15% triethylamine in methylene chloride (two times for 7 minutes each); (3) dimethylformamide (two times); (f) methylene chloride (five times). A similar sequence is used for deprotection and neutralization after each coupling. The following amino acid residues are introduced onto the above resin consecutively: t-Boc-L-proline (5 m moles), t-Boc-N$^g$-tosyl-L-arginine (5 m moles), t-Boc-L-leucine (5 m moles), t-Boc-N -2-chlorobenyloxycarbonyl-D-lysine (4 m moles), t-Boc-O2,6-dichlorobenzyl-L-tyrosine (4 m moles), t-Boc-O-benzyl-L-serine (4 m moles), t-Boc-L-tryptophan (4 m moles), L-pyroglutamic acid (3 m moles). All the couplings are carried out in a mixture of methylene chloride and dimethylformamide (3:1) for 18 hours at ambient temperature using a 10% excess of diisopropylcarbodiimide, which is added in two portions over a one hour period. Each coupling is then effected a second time, after filtering and washing with methylene chloride, using one half the original quantities of reactants and allowing a reaction time of 3 hours. The washings between couplings are the same as those described above after the coupling of t-Boc-glycine.

The washed resin is dried in vacuo (6.7 g).

EXAMPLE 2

L-Pyroglutamyl-L-tryptophyl-L-seryl-L-tyrosyl-D-lysyl-L-leucyl-L-arginyl-L-prolyl-glycinamide The above described preparation obtained in Example 1 is treated in vacuo with liquid anhydrous hydrogen fluoride (50 ml) and anisole (10 ml) at ambient temperature for 1 hour. The hydrogen fluoride is removed as quickly as possible under reduced pressure, and the residue is washed with ether. The remaining residue is extracted with 0.5N acetic acid and lyophylized to leave the above titled product (1.87 g).

EXAMPLE 3

Purification and characterization of -pyroglutamul-L-tryptophyl-L-seryl-L-tyrosyl-D-lysyl-L-leucyl-L-arginyl-L-prolyl-glycinamide The above titled crude product obtained in Example 2 is purified as follows:

1.87 G of this product in 3 ml of 0.5 N acetic acid is applied to a column (2.9 cm in a diameter and 150 cm in height) with a bed of Sephadex G-15 previously equilibrated with 0.5 N acetic acid and eluted with that solvent. Fractions of 3.5 ml each are taken and analysis of the column effluent is carried out by use of the Folin-Lowry color reaction on every third fraction. Four main peptide containing fractions are obtained: (A) 140–149 (358 mg); (B) 150–154 (241 mg); (C) 155–159 (180 mg); (D) 160–170 (237 mg). Fractions B and C (421 mg) are shown by thin layer chromatography systems BWAP (4:2:1:1) (n-butanol:water:acetic acid:pyridine) and BWP (3:1:5:2) (n-butanol:water:pyridine) to contain the same major material. They are combined and applied in 1 ml of the upper phase of n-butanol:water:acetic acid (b 4:5:1) to a column (2.9 cm in diameter and 90 cm in height) with a bed of Sephadex G-25 fine previously equilibrated with first the lower phase of that system and then the upper phase. The column is eluted with the upper phase and fractions of 2 ml each are taken. The column effluent is monitored as described before. Four main peptide containing fractions are obtained: (C) 205–214 (90 mg); (D) 215–224 (92 mg); (E) 225–234 (91 mg); (F) 235–245 (39 mg). Fraction E is homogenous by thin layer chromatography systems BWAP (4:2:1:1) and BWP (3:1.5:2) on silica gel ($R_f$ 0.51 and 0.05 respectively. $[\alpha]_D^{25} = -31.92$ (c 1.02%, 1% AcOH).

After hydrolysis of the peptide in 5 N HCl containing 4% thioglycolic acid for 20 hours at 110°C in a closed system under nitrogen, the following values for the amino acid residues are obtained: Glu 1.04; Trp 0.79; Ser 0.93; Tyr 1.05; Lys 1.00; Leu 0.95; Arg 1.02; Pro 0.95; Gly 1.13.

The compounds of formula I possess anti-ovulatory activity and hence are potentially useful in inhibiting fertility in female mammals. In vivo tests were conducted with female rats (225 to 250 grams body weight). Ovulation inhibition was achieved in all of the rats tested at a dose of about 24 mg/kg using the compound of Example 3. The test was conducted with mature Sprague-Dawley rats, unanesthetized, proestrous rats. On the afternoon of proestrous, each rat in the test group received six subcutaneous injections of the acetate salt of formula I in corn oil, each injection being given a half hour following the previous injection. The rats are sacrificed the next morning and the number of animals ovulating and the number of ova shed are recorded following the procedure described by E. S. France, *Neuroendocrinology* 6, pp 77–89 (1970). The absence of or a significant decrease in the number of ova is the criterion for an anti-ovulation effect. At a dose of 1 mg per injection complete inhibition of ovulation was achieved.

The compounds of formula I can be administered to mammals intravenously, subcutaneously, intramuscularly or orally for fertility inhibition and ovulation control since LH is known to trigger ovulation in mammals [See Schally et al., *Am. J. Obstet. Gynecol.* pp 423–442, Oct. 1972]. The effective dosage will vary with the form of administration and the particular species of mammal to be treated. A typical dosage is a physiological saline solution containing a compound of formula I administered in a dose range of between about 20 to 30 mg/kg of body weight. Oral administration may be in either solid or liquid form.

What is claimed is:

1. A compound selected from the class consisting of

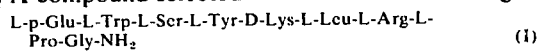

and

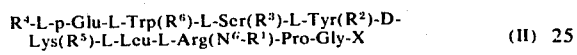

and its non-toxic salts; wherein $R^1$ is a protecting group for the $N^\delta$, $N^\omega$ and $N^{\omega'}$ nitrogen atoms of arginine selected from the group consisting of nitro, tosyl, benzyloxycarbonyl, adamantyloxycarbonyl and tert-butyloxycarbonyl or $R^1$ is hydrogen;

$R^2$ is a protecting group for the phenolic hydroxyl group of tyrosine selected from the group consisting of tert-butyl, tetrahydropyranyl, trityl, benzyl, 2,6-dichlorobenzyl, 4-bromobenzyloxycarbonyl and benzyloxycarbonyl or $R^2$ is hydrogen;

$R^3$ is a protecting group for the alcoholic hydroxyl group of serine and is selected from the group consisting of acetyl, benzoyl, tetrahydropyranyl, tert-butyl, trityl, 2,6-dichlorobenzyl and benzyl or $R^3$ is hydrogen;

$R^4$ is selected from the group consisting of hydrogen or an α-amino protecting group;

$R^5$ is a protecting group for the side chain amino substituent of lysine selected from the class consisting of 2-chlorobenzyloxycarbonyl, benzyloxycarbonyl, tosyl, t-amyloxycarbonyl, t-butyloxycarbonyl; or $R^5$ is hydrogen;

$R^6$ is selected from the class consisting of hydrogen and formyl; and

X is selected from the group consisting of $NH_2$, O-(lower)-alkyl, O-benzyl and an anchoring bond linked to a solid polystyrene resin represented by one of the formula

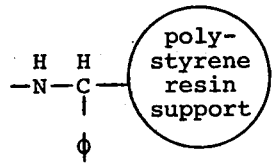

and

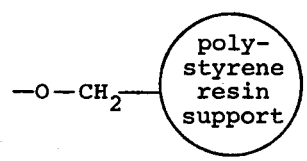

wherein said polystyrene resin is cross linked through the phenyl group on each second carbon atom of the alkyl chain of said polystyrene and said symbol φ means phenyl, with the proviso that at least one of $R^1$, $R^2$, $R^3$, $R^5$ and $R^6$ is a protecting group.

2. A compound according to formula II of claim 1 wherein X is $NH_2$.

3. A compound according to formula II of claim 1 wherein $R^4$ is hydrogen and X is

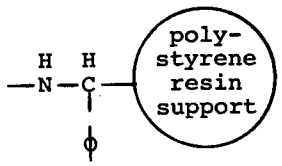

4. A compound according to claim 3 wherein $R^1$ is tosyl, $R^2$ is 2,6-dichlorobenzyl, $R^3$ is benzyl, $R^5$ is 2-chlorobenzyloxycarbonyl and $R^6$ is hydrogen.

5. A compound according to claim 1 which is selected from L-Pyroglutamyl-L-tryptophyl-L-seryl-L-tyrosyl-D-lysyl-L-leucyl-L-arginyl-L-prolyl-glycinamide and its non-toxic acid addition salts.

* * * * *

Notice of Adverse Decision in Interference

In Interference No. 100,096, involving Patent No. 3,937,695, D. Sarantakis, P-GLU-TRP-SER-TYR-D-LYS-LEU-ARG-PRO-GLY-$NH_2$, AND INTERMEDIATES, final judgment adverse to the patentee was rendered Apr. 2, 1980, as to claim 1.

[*Official Gazette July 22, 1980.*]